_United States Patent_ [19]

Marsella

[11] Patent Number: 4,709,034
[45] Date of Patent: Nov. 24, 1987

[54] PROCESS FOR THE SYNTHESIS OF HYDROXYALKYL AMINES AND HYDROXYALKYL PIPERAZINES

[75] Inventor: John A. Marsella, Allentown, Pa.

[73] Assignee: Air Products and Chemicals, Inc., Allentown, Pa.

[21] Appl. No.: 829,680

[22] Filed: Feb. 14, 1986

[51] Int. Cl.$^4$ .................. C07D 241/04; C07D 85/18
[52] U.S. Cl. .................................. 544/401; 544/358; 544/398; 564/478; 564/479; 564/480
[58] Field of Search ................ 544/358, 401, 398; 564/478, 479, 480

[56] References Cited

U.S. PATENT DOCUMENTS

| 3,137,730 | 6/1964 | Fitz-William | 260/585 |
| 4,123,462 | 10/1978 | Best | 260/585 |
| 4,322,530 | 3/1982 | Jachimowicz | 544/358 |

FOREIGN PATENT DOCUMENTS 813957  5/1959  United Kingdom .

OTHER PUBLICATIONS

Jachimowicz et al., J. Org. Chem., vol. 47, pp. 445–447 (1982).
J.A.C.S., vol. 101, pp. 7419–7421 (1979).
Ethylenediamine by Low-Pressure Ammonolysis of Monoethanolamine, C. M. Barnes and H. F. Rase.
Comprehensive Organometallic Chemistry, The Synthesis, Reactions & Structures of Organometallic Compounds.

_Primary Examiner_—Donald G. Daus
_Assistant Examiner_—Cecilia Shen
_Attorney, Agent, or Firm_—Mark L. Rodgers; William F. Marsh; James C. Simmons

[57] ABSTRACT

The present invention comprises a process for the synthesis of hydroxyalkyl amines, hydroxyalkyl piperazines, or alkyl piperazines from alkylene glycols and ammonia or alkyl amines using a substantially soluble transition metal carbonyl complex catalyst precursor.

22 Claims, 6 Drawing Figures

PROCESS FOR THE SYNTHESIS OF HYDROXYALKYL AMINES AND HYDROXYALKYL PIPERAZINES

SUMMARY OF THE INVENTION

The present invention comprises a process for the synthesis of hydroxyalkyl amines, hydroxyalkyl piperazines or alkyl piperazines from reaction mixtures of alkylenes glycols and ammonia or alkyl amines. These reactions are catalyzed using ruthenium-based substantially soluble catalytic systems.

BACKGROUND OF THE INVENTION

Current methods of synthesizing ethanol-amines involve reactions of ethylene oxide and ammonia. Because of its flammability, toxicity-(permissible worker exposure levels are 1 ppm), and volatility, an alternative feedstock to ethylene oxide would be desirable.

The prior art contains teachings of the use of ethylene glycol (EG) as a feedstock for ammonolysis reactions using both supported and non-supported catalysts. No known references disclose the use of soluble catalyst systems. Those references which teach use of ethylene glycol, however, always operate their processes under ammonia-rich conditions in order to avoid the predominant side reactions and production of undesirable cyclic byproducts which occur under ammonia-lean conditions.

Previous methods involving reactions of ethylene glycol and ammonia are typified by U.S. Pat. No. 3,137,730 to Fitz-William. As taught by Fitz-William, a large excess of ammonia (i.e., at least 5 mols $NH_3$ per mol glycol) is reacted with ethylene glycol over a heterogeneous copper/nickle catalyst supported on alumina. The product of such a reaction is ethylenediamine rather than ethanolamines. In fact, the results reported by Fitz-William fail to indicate any production of ethanol amines.

U.S. Pat. Nos. 4,123,462 to Best also teaches the reaction of large excesses of ammonia with ethylene glycol. As taught by Best, a heterogeneous nickel-rhenium catalyst is used to produce, among other products, ethylenediamine and piperazine (using $EG:NH_3$ ratios of from 1:4 to 1:20). Best notes a production of ethanolamine (column 18, line 61-3) but quantifies this production only as a relative GC area ratio to the production of piperazine. Furthermore, only monoethanolamine (MELA) is reported by Best as a reaction product.

British Pat. No. 813,957 describes the production of 2,5-dimethyl piperazine from a 2:1 mixture of ammonia and propylene glycol over a heterogeneous Cu/Cr/Ni catalyst. Such a reaction typifies the production of cyclic products in ammonia-lean reaction systems. Because of this tendency to produce cyclic products under low ammonia conditions, the prior art has taught the use of excess ammonia (see "Ethylenediamine by Low-Pressure Ammonolysis of Monoethanolamine", *Ind. Eng. Chem. Prod. Res. Dev.* 1981, 20, 399-407 by C. M. Barnes and H. F. Race). As taught by Barnes and Race, the prior art suggests two possible paths for reactions of ethylene glycol with ammonia. At high ammonia to ethylene glycol ratio, ethylenediamine appears to be a predominant product, while at lower ratios, piperazine might be expected to predominate.

BRIEF DESCRIPTION OF THE INVENTION

The present invention uses substantially soluble transition metal carbonyl catalysts in the ammonolysis of alkylene glycols to produce hydroxyalkyl amines, hydroxyalkyl piperazines or alkyl piperazines. High ammonia-to-ethylne glycol ratios are not necessary to the synthesis and have been shown to reduce reaction rates undesirably.

DETAILED DESCRIPTION OF THE INVENTION

Figure 1:
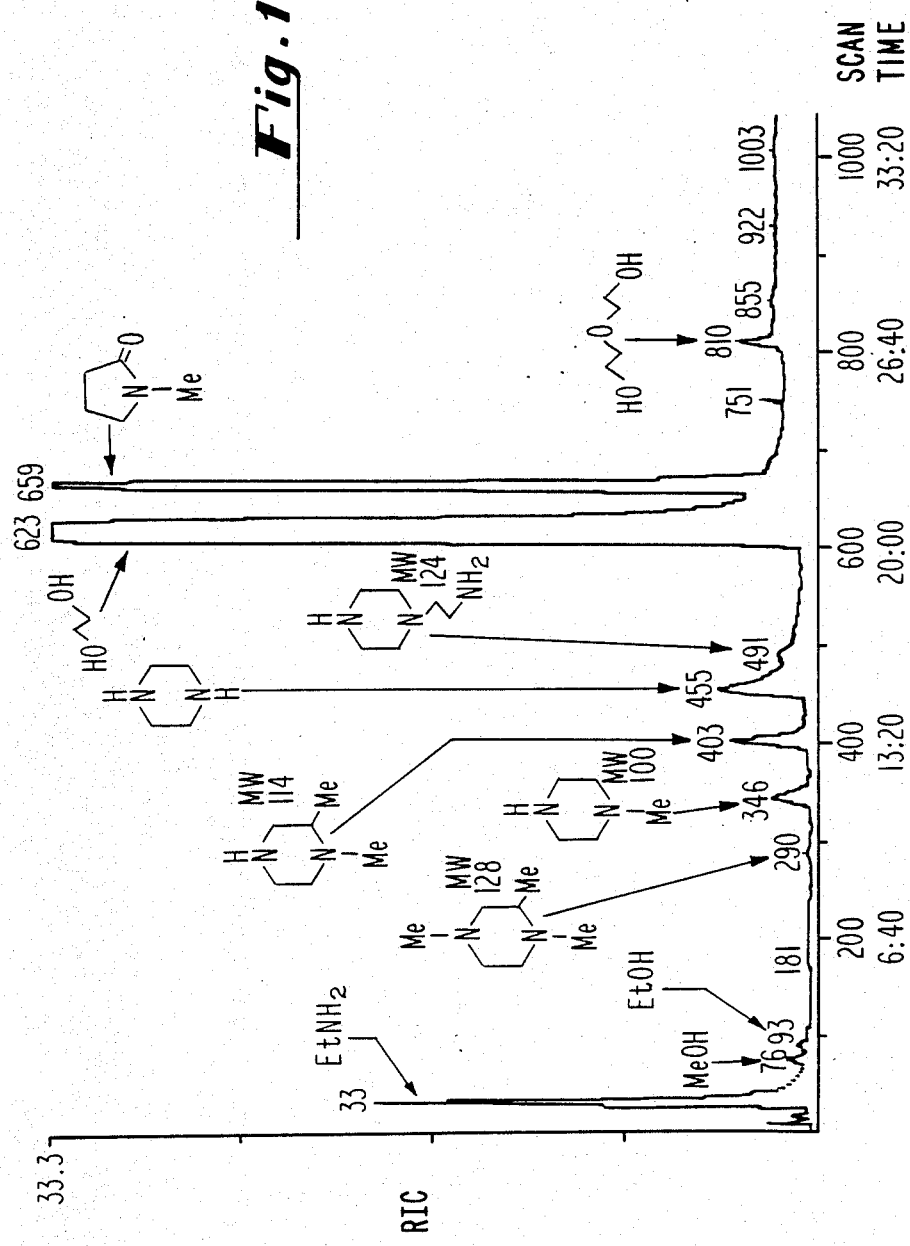
FIG. 1 is a Gas Chromatograph/Mass Spectrograph Trace illustrating the products resulting from a reaction of EG and $NH_3$ catalyzed by 5% Ru/C heterogeneous catalyst.

According to the present invention, alkylene glycols and ammonia or an alkyl amine are reacted in the presence of a substantially soluble transition metal carbonyl complex (preferably ruthenium carbonyl) catalyst to form hydroxyalkyl amines, alkyl piperazines or hydroxyalkyl piperazines. A typical synthesis employs a ruthenium carbonyl catalyst precursor such as $Ru_3(CO)_{12}$. Other catalyst precursors employed include the other periodic table second and third-row carbonyls (e.g. $H_4Ru_4(CO)_{12}$, $Os_3(CO)_{12}$, $Ir_4(CO)_{12}$, $Rh_6(CO)_{16}$, $Re_2(CO)_{10}$). Also suitable are compounds which may be converted to these carbonyls in situ. For example, $RuCl_3 \cdot xH_2O$ may be treated with CO and $H_2$; see Bruce, *Ruthenium Carbonyls and Related Compounds,* Comprehensive Organometallic Chemistry, Wilkinson et al., ed., Pergamon Press (1982).

The synthesis of monoethanolamine (MELA) according to the present invention is thought to proceed according to reaction (I), which is more commonly written according to the convention of reaction (II). Subsequent reactions also catalyzed include the synthesis of diethanolamine (DELA) according to mechanisms similar to reaction (III). Similarly, production of triethanolamine (TELA) is thought to proceed according to the mechanism of reaction (IV).

$$HOCH_2CH_2OH + NH_3 \rightarrow HOCH_2CH_2NH_2 + H_2O \quad (I)$$

$$EG + NH_3 \rightarrow MELA + H_2O \quad (II)$$

$$MELA + EG \rightarrow DELA + H_2O \quad (III)$$

DELA + EG → TELA + H₂O        (IV)

The synthesis of N-(hydroxyethyl)piperazine (HEP) may proceed according to the steps detailed in reactions ($V_a$-$V_d$). The overall reaction for the synthesis of HEP is represented as equation ($V_e$). Similarly, the production of N-N'-bis(hydroxyethyl)piperazine (BHEP) is thought to proceed according to equation (VI).

EG + NH₃ ⟶ MELA + H₂O        ($V_a$)

MELA + MELA ⟶ NH₂CH₂CH₂NHCH₂CH₂OH + H₂O        ($V_b$)
hydroxyethylethylenediamine
(HEEDA)

HEEDA + MELA ⟶        ($V_c$)

NH₂CH₂CH₂NHCH₂CH₂NHCH₂CH₂OH + H₂O
2-((2-((2-aminoethyl)amino)ethyl)amino)ethanol
(AAEAE)

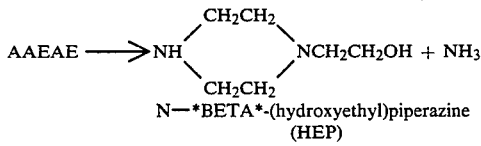
N—*BETA*-(hydroxyethyl)piperazine
(HEP)

3EG + 2NH₃ ⟶ HEP + 5H₂O        ($V_e$)

HEP + EG ⟶ N—N'—bis(hydroxyethyl)piperazine        (VI)
BHEP

There are a large number of synthetic routes in the ammonolysis of ethylene glycol to HEP. Many proceed through reactions similar to that shown in equations (VIIa-b).

DELA + MELA → bis(hydroxyethyl)ethylenediamine        (VIIa)

bis(hydroxyethyl)ethylenediamine → HEP + H₂O        (VIIb)

GENERAL EXPERIMENTAL PROCEDURE

Reactions were carried out in either a 175 cc autoclave constructed of Hastelloy C stainless steel, and equipped with an impeller-type stirring device and a thermocouple well, or in a 50 cc pressure bomb which was magnetically stirred. Reaction mixtures typically exhibited a molar ratio of EG:NH₃ of from 10:1 to 1:3, the preferred range being from 3:1 to 1:3. Reactions were carried out under hydrogen pressures of 0–1000 psig (250–750 psig was preferred) at temperatures of 150°–300° C. (200°–220° C. was preferred) for a two hour period.

Ethylene glycol was obtained as 99%+ pure from Aldrich. Anhydrous-grade ammonia was supplied by Air Products and Chemicals, Inc. and carbonyl catalyst complexes were obtained from either Strem or Alpha. The supported catalysts employed (5% Ru/C and 5% Ru/Al₂O₃) were obtained from Engelhard.

In order to obtain mass balances for the various reactions, the 50 cc pressure bomb had its head-gases removed from the reactor and vented through 2M HCl solution. Ammonia lost through venting was then determined by weight gain of the acid solution.

For reactions where the EG:NH₃ charge ratio exceeded about 2, solutions of known ammonia concentrations in ethylene glycol were made by bubbling ammonia through the ethylene glycol and monitoring the weight gained. This solution was then typically added directly to the catalyst in a reactor which had been filled with dry nitrogen gas. The reactor was subsequently sealed, pressurized, and heated to the desired pressure and temperature. Reaction times were uniformly measured from the time of obtaining desired temperature. For ammonia rich reactions, the reactor was loaded with catalyst and ethylene glycol, and flushed with N₂. A known weight of ammonia was then condensed into the reactor from a previously weighed sample bomb. The amount of ammonia in the reactor was determined by diffence from weighing the sample bomb.

After the end of the desired reaction time, the reactor was typically cooled and vented. Analysis of product components was by gas chromatography on a packed column which was well known for its ability to analyze polyamines and morpholine. Results of these experimental runs are tabulated in the example tables below.

The following examples demonstrate various parameters relating to the synthesis process of the present invention. These examples also serve to illustrate the relative effectiveness of several catalytic systems, and the applicability of the synthetic process of the present invention to synthesis involving alkylamines in addition to ammonia.

EXAMPLE 1

Typical Reaction of EG and NH₃ using Ru₃(CO)₁₂ Catalyst Precursor

Reaction of: EG and NH₃
Reaction Temperature: 200° C.
Reaction Time: 2 hours; NH₃ Charge: 5.98 g; EG Charge: 49.92 g
H₂ Pressure at 25° C.: 510 psig; EG:NH₃ Molar Ratio: 2.3:1
Results:

| Product | GC Area % | Weight (grams) | Selectivity NH₃ Conversion 80% | EG 71% |
|---------|-----------|----------------|-------------------------------|--------|
| MELA    | 3.20      | 1.59           | 9                             | 5      |
| DELA    | 11.34     | 7.13           | 24                            | 24     |
| TELA    | 3.85      | 4.28           | 10                            | 15     |
| HEP     | 0.19      | 0.05           | 3                             | 2      |
| BHEP    | 4.75      | 5.19           | 21                            | 21     |

Catalyst: 0.25 g Ru₃(CO)₁₂; Reactor: 175 cc Autoclave

EXAMPLE 2

Comparative Example using a Commercial Heterogeneous Ru Catalyst

Reaction of: EG and NH₃
Reaction Temperature: 203° C.
Reaction Time: 2 hours; H₂ Charge: 6.0 g; EG Charge: 55.5 g
H₂ Pressure at 25° C.: 530 psig; EG:NH₃ Molar Ratio: 2.5:1
Results:
No hydroxyalkyl amines observed by GC/MS. Principal products were ethylamine, piperazine, and methylpiperazines. (See FIG. 1 for full identification of products of reaction.)

Catalyst: 1.5 g of 5% Ru on Carbon (Engelhard); Reactor: 175 cc Autoclave

EXAMPLE 3

Comparative Example using Commercial Heterogeneous Catalysts—Tert-Butylamine and EG Reaction of: Tert-Butylamine and EG
Reaction Temperature: 200°–205° C.
Reaction Time: 2 hours
H$_2$ Pressure at 25° C.: 500 psig; EG:t-BuNH$_2$ Molar Ratio: 2.9:1
Reaction:

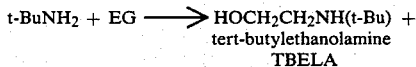
tert-butylethanolamine
TBELA

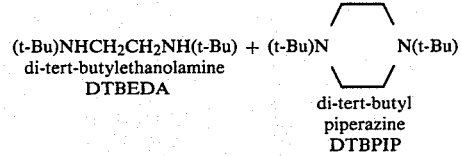
di-tert-butylethanolamine
DTBEDA
di-tert-butyl piperazine
DTBPIP

Results:

| Catalyst | Conversion (%) | Selectivities | | | Acc. (%) |
|---|---|---|---|---|---|
| | | TBELA | DTBEDA | DTBPIP | |
| 5% R/Al$_2$O$_3$ | 52 | 35 | 46 | 10 | 91 |
| 5% Ru/C | 25 | 27 | 31 | 41 | 99 |
| 2% Ru/TiO$_2$ | 18 | 14 | 28 | 17 | 59 |
| 60% Co/Kiesel guhr* | 15 | 24 | 1 | 0.5 | 25 |

Reactor: 50 cc Pressure Bomb
*0.5 Wt. % Catalyst
Note: Acc. is Accountability of amine (% of amine accounted-for by all products.)

EXAMPLE 4

Reactions of EG and Primary Amines

Reaction of: EG and Various Primary Amines
Reaction Temperature: 200°–205° C.
Reaction Time: 2 hours
H$_2$ Pressure at 25° C.: 500 psig
Reactions:

H$_2$NR+EG→RELA+DREDA+DRPIP

Results:

| Amine | Amine:EG | Conv. % | Selectivities (%) | | | Acc. % |
|---|---|---|---|---|---|---|
| | | | RELA | DREDA | DRPIP | |
| MeNH$_2$ | 0.49:1 | 57 | 10 | 9 | 31 | 50 |
| MeNH$_2$ | 0.35:1 | 78 | 3 | 2 | 20 | 25 |
| MeNH$_2$ | 0.50:1 | 73 | 12 | — | 45 | 57 |
| MeNH$_2$ | 0.44:1 | 68 | 12 | 5* | 40 | 57 |
| i-BuNH$_2$ | 0.31:1 | 75 | 43 | 21 | 20 | 84 |
| i-BuNH$_2$ | 0.33:1 | 69 | 26 | 7 | 27 | 60 |
| i-BuNH$_2$ | 0.32:1 | 76 | 43 | 20 | 19 | 82 |
| s-BuNH$_2$ | 0.37:1 | 91 | 34 | 7 | 28 | 69 |
| s-BuNH$_2$ | 0.32:1 | 68 | 27 | 33 | 26 | 86 |
| t-BuNH$_2$ | 0.35:1 | 34 | 12 | 84 | 3 | 99 |
| t-BuNH$_2$ | 0.33:1 | 100 | 42 | 37 | 14 | 93 |

Catalyst: 0.00175M Ru; Reactor: 175 cc Autoclave
Examples 5–22 represent the actual data plotted in FIGS. 2–5. For the purpose of graphing the selectivities based on different reaction conditions, selectivities were normalized with respect to the 5 major products according to the following formula:

$$(\text{Norm. Sel.})_i = \frac{(\text{Sel.})_i}{(\text{Sel.})_{MELA} + (\text{Sel.})_{DELA} + (\text{Sel.})_{TELA} + (\text{Sel.})_{HEP} + (\text{Sel.})_{BHEP}} \times 100$$

where i represents a given product (MELA, DELA, TELA, HEP, or BHEP) and $$(\text{Sel.})_i = \frac{\text{Yield of } i}{\text{conversion}} \times 100$$

Figure 2:
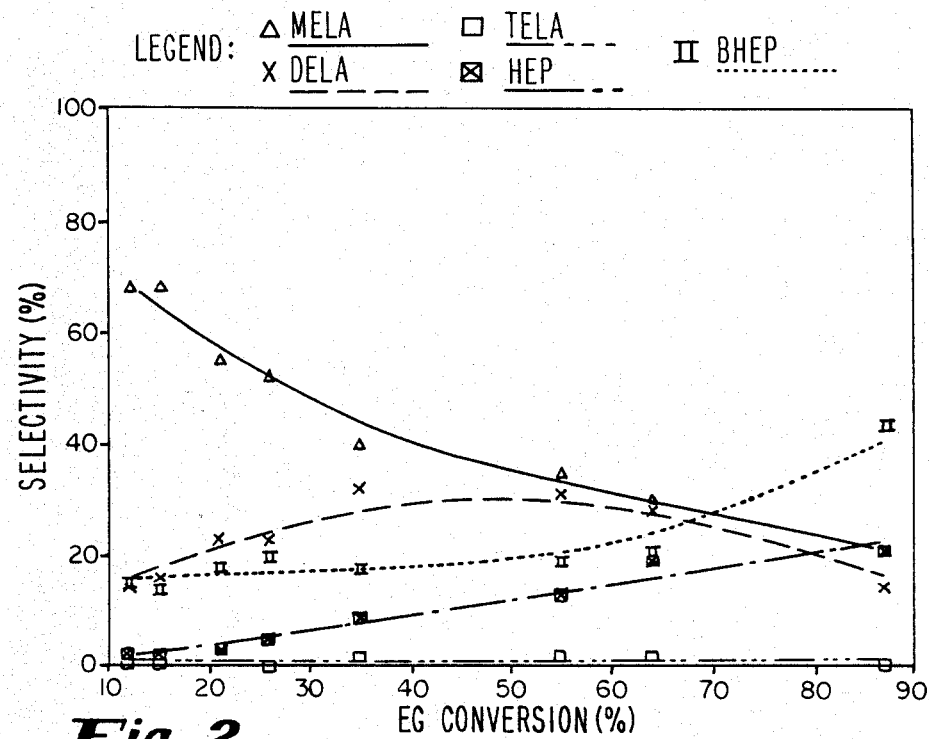
FIG. 2 is a plot of conversion of EG against selectivity for each of the 5 major reaction products produced at an $EG:NH_3$ charge ratio of about 0.5:1 catalyzed by $Ru_3(CO)_{12}$ catalyst precursor.
Figure 3:
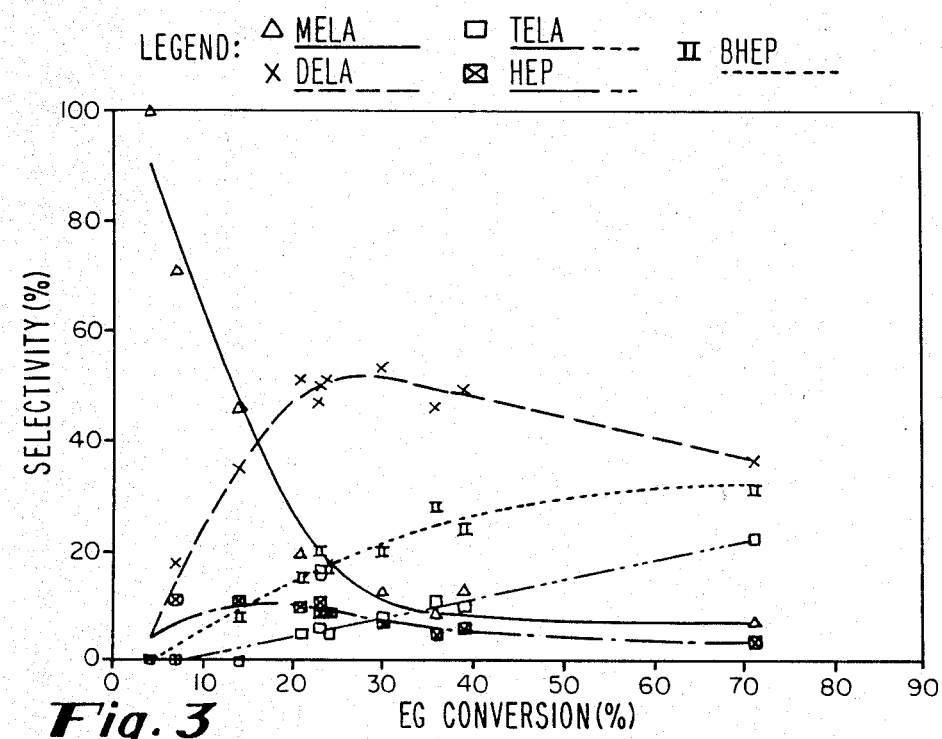
FIG. 3 is a plot of conversion of EG against selectivity for each of the 5 major reaction products produced at an $EG:NH_3$ charge ratio of about 2.5:1 catalyzed by $Ru_3(CO)_{12}$ catalyst precursor.

Comparison of FIGS. 2 and 3 indicates that useful conversion to nitrogen-containing alkyl products does not require the ammonia-rich conditions of the prior art. While ammonia-rich mixtures appear to favor DELA and TELA over MELA for EG conversions greater than 15%, the ammonia-lean reactions favor HEP and BHEP. In direct contrast to the teachings of the prior art, ammonia-lean conditions do not result in notable increases in undesired cyclic by-products and decreased selectivities.

Figure 4:
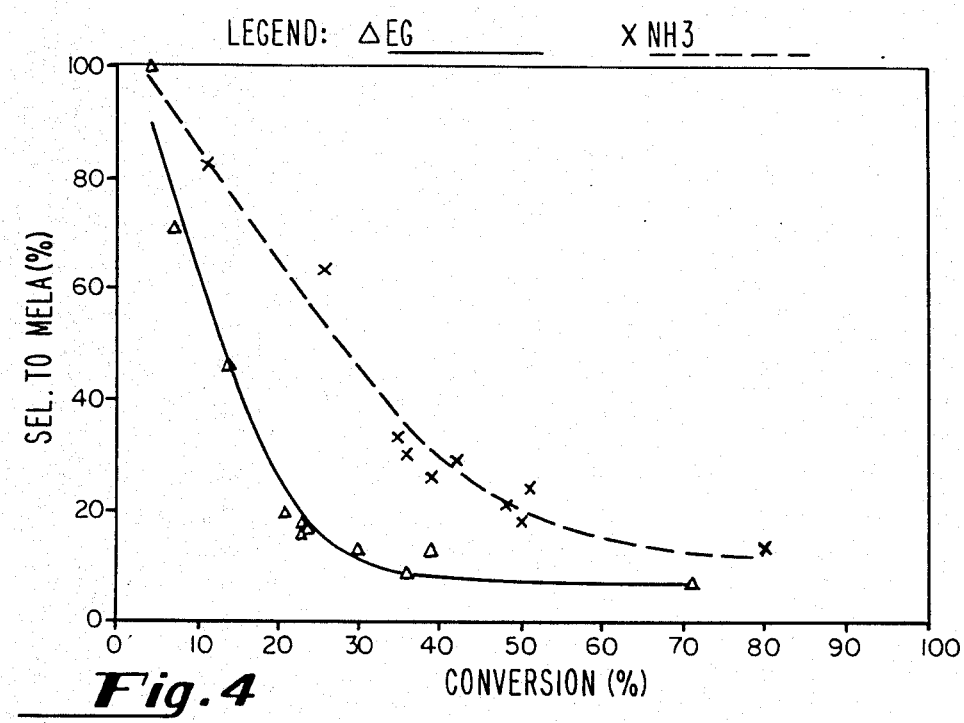
FIG. 4 is a plot of conversion of both EG and $NH_3$ against normalized selectivity to MELA catalyzed by $Ru_3(CO)_{12}$ catalyst precursor.
Figure 5:
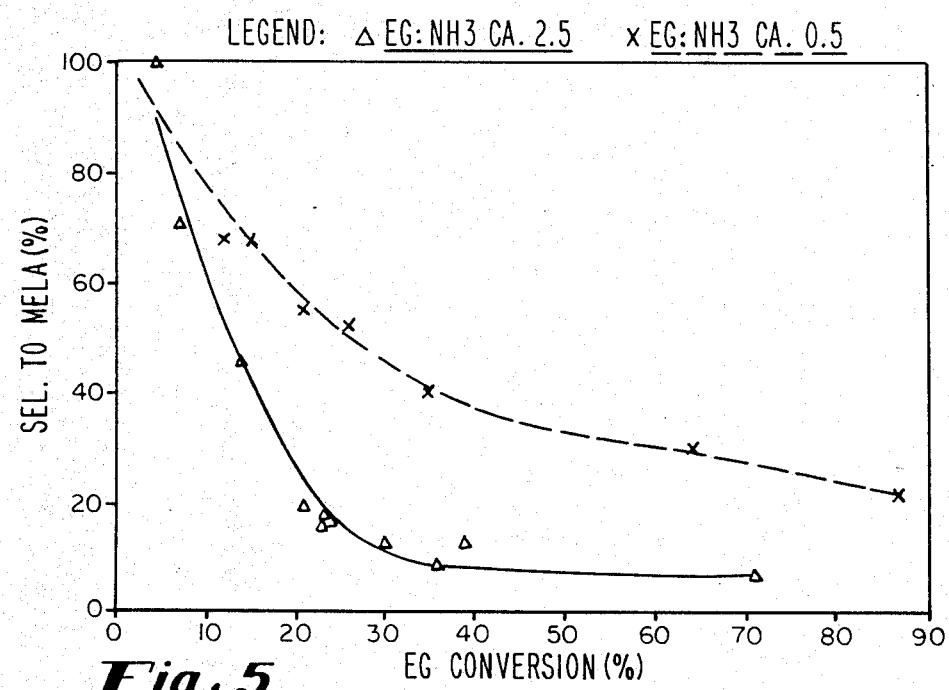
FIG. 5 is a plot of conversion of EG against normalized selectivity to MELA for $EG:NH_3$ charge ratios of 0.5:1 and 2.5:1 catalyzed by $Ru_3(CO)_{12}$ catalyst precursor.

FIG. 4 demonstrates the expected inverse relationship between selectivity to MELA and conversion of both EG and NH$_3$. As expected, higher conversions of EG (which result in greater production of the other product species) tends to reduce selectivity to MELA. This effect is thought to be due to consumption of MELA in subsequent reactions with EG to produce DELA, TELA, etc.

Figure 6:
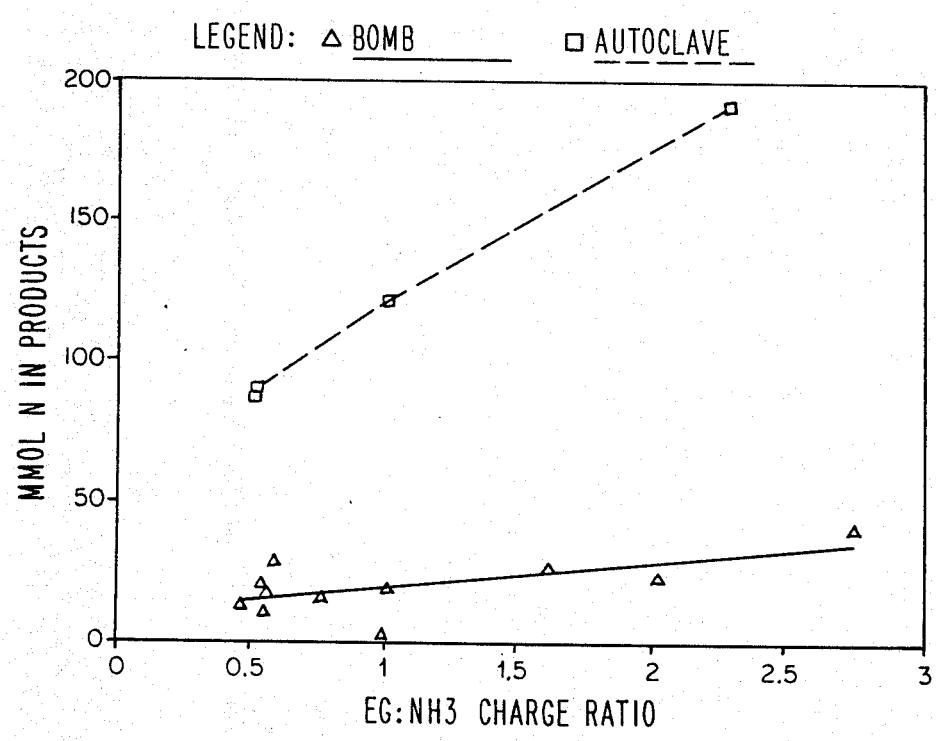
FIG. 6 is a plot of $EG:NH_3$ charge ratio against amount of nitrogen-containing products produced catalyzed by $Ru_3(CO)_{12}$ catalyst precursor.

Finally, FIG. 6 demonstrates the relationship of absolute production of nitrogen-containing alkyls to EG:NH$_3$ (reactor) charge ratio. Contrary to the teachings of the prior art, at higher EG:NH$_3$ ratios, production of nitrogen-containing alkyls is enhanced.

EXAMPLE 5

Reaction of: EG and NH$_3$
Reaction Temperature: 201° C.
Reaction Time: 2 hours; NH$_3$ Charge: 2.49 g; EG Charge: 22.21 g
H$_2$ Pressure at 25° C.: 0; EG:NH$_3$ Molar Ratio: 2.44:1
Results:

| Product | Weight (grams) | Selectivity | |
|---|---|---|---|
| | | NH$_3$ Conversion 26% | EG 14% |
| MELA | 0.55 | 24 | 17 |
| DELA | 0.35 | 9 | 13 |
| TELA | 0.00 | 0 | 0 |
| HEP | 0.08 | 3 | 4 |
| BHEP | 0.06 | 2 | 3 |

Catalyst: Ru$_3$(CO)$_{12}$ (100 mg); Reactor: 50 cc Pressure Bomb

EXAMPLE 6

Reaction of: EG and NH$_3$
Reaction Temperature: 201° C.
Reaction Time: 2 hours; NH$_3$ Charge: 2.59 g; EG Charge: 22.79 g H$_2$ Pressure at 25° C.: 280 psig; EG:NH$_3$ Molar Ratio: 2.41:1
Results:

| Product | Weight (grams) | Selectivity NH$_3$ Conversion 51% | EG Conversion 39% |
|---|---|---|---|
| MELA | 0.83 | 18 | 9 |
| DELA | 2.62 | 32 | 35 |
| TELA | 0.49 | 4 | 7 |
| HEP | 0.25 | 5 | 4 |
| BHEP | 1.03 | 15 | 17 |

Catalyst: Ru$_3$(CO)$_{12}$ (100 mg); Reactor: 50 cc Pressure Bomb

EXAMPLE 7

Reaction of: EG and NH$_3$
Reaction Temperature: 201° C.
Reaction Time: 2 hours; NH$_3$ Charge: 2.36 g; EG Charge: 23.58 g
H$_2$ Pressure at 25° C.: 530 psig; EG:NH$_3$ Molar Ratio: 2.74:1
Results:

| Product | Weight (grams) | Selectivity NH$_3$ Conversion 42% | EG Conversion 24% |
|---|---|---|---|
| MELA | 0.71 | 20 | 13 |
| DELA | 1.85 | 30 | 39 |
| TELA | 0.19 | 2 | 4 |
| HEP | 0.26 | 7 | 7 |
| BHEP | 0.53 | 10 | 14 |

Catalyst: Ru$_3$(CO)$_{12}$ (100 mg); Reactor: 50 cc Pressure Bomb

EXAMPLE 8

Reaction of: EG and NH$_3$
Reaction Temperature: 201° C.
Reaction Time: 2 hours; NH$_3$ Charge: 2.41 g; EG Charge: 21.99 g
H$_2$ Pressure at 25° C.: 750 psig; EG:NH$_3$ Molar Ratio: 2.50:1
Results:

| Product | Weight (grams) | Selectivity NH$_3$ Conversion 35% | EG Conversion 21% |
|---|---|---|---|
| MELA | 0.71 | 24 | 16 |
| DELA | 1.57 | 30 | 41 |
| TELA | 0.15 | 2 | 4 |
| HEP | 0.26 | 8 | 8 |
| BHEP | 0.38 | 9 | 12 |

Catalyst: Ru$_3$(CO)$_{12}$ (100 mg); Reactor: 50 cc Pressure Bomb

EXAMPLE 9

Reaction of: EG and NH$_3$
Reaction Temperature: 203° C.
Reaction Time: 2 hours; NH$_3$ Charge: 2.36 g; EG Charge: 22.21 g
H$_2$ Pressure at 25° C.: 1005 psig; EG:NH$_3$ Molar Ratio: 2.58:1
Results:

| Product | Weight (grams) | Selectivity NH$_3$ Conversion 39% | EG Conversion 23% |
|---|---|---|---|
| MELA | 0.70 | 21 | 14 |
| DELA | 1.83 | 33 | 42 |
| TELA | 0.21 | 3 | 5 |
| HEP | 0.36 | 10 | 10 |
| BHEP | 0.65 | 14 | 18 |

Catalyst: Ru$_3$(CO)$_{12}$ (100 mg); Reactor: 50 cc Pressure Bomb

EXAMPLE 10

Reaction of: EG and NH$_3$
Reaction Temperature: 201° C.
Reaction Time: 1 hour; NH$_3$ Charge: 2.47 g; EG Charge: 22.06 g
H$_2$ Pressure at 25° C.: 525 psig; EG:NH$_3$ Molar Ratio: 2.44:1
Results:

| Product | Weight (grams) | Selectivity NH$_3$ Conversion 36% | EG Conversion 23% |
|---|---|---|---|
| MELA | 0.76 | 24 | 15 |
| DELA | 1.80 | 33 | 42 |
| TELA | 0.21 | 3 | 5 |
| HEP | 0.28 | 8 | 8 |
| BHEP | 0.51 | 11 | 14 |

Catalyst: Ru$_3$(CO)$_{12}$ (100 mg); Reactor: 50 cc Pressure Bomb

EXAMPLE 11

Reaction of: EG and NH$_3$
Reaction Temperature: 201° C.
Reaction Time: 3 hours; NH$_3$ Charge: 2.38 g; EG Charge: 22.05 g
H$_2$ Pressure at 25° C.: 540 psig; EG:NH$_3$ Molar Ratio: 2.54:1
Results:

| Product | Weight (grams) | Selectivity NH$_3$ Conversion 50% | EG Conversion 36% |
|---|---|---|---|
| MELA | 0.72 | 17 | 9 |
| DELA | 2.95 | 40 | 44 |
| TELA | 0.65 | 6 | 10 |
| HEP | 0.29 | 6 | 5 |
| BHEP | 1.51 | 25 | 27 |

Catalyst: Ru$_3$(CO)$_{12}$ (100 mg); Reactor: 50 cc Pressure Bomb

EXAMPLE 12

Reaction of: EG and NH$_3$
Reaction Temperature: 202° C.
Reaction Time: 5 hours; NH$_3$ Charge: 2.345 g; EG Charge: 22.1 g
H$_2$ Pressure at 25° C.: 520 psig; EG:NH$_3$ Molar Ratio: 2.58:1

Results:

| Product | Weight (grams) | Selectivity NH₃ Conversion 11% | EG Conversion 7% |
|---|---|---|---|
| MELA | 0.29 | 32 | 20 |
| DELA | 0.06 | 4 | 5 |
| TELA | 0.00 | 0 | 0 |
| HEP | 0.03 | 3 | 3 |
| BHEP | 0.00 | 0 | 0 |

Catalyst: $Ru_3(CO)_{12}$ (100 mg); Reactor: 50 cc Pressure Bomb

EXAMPLE 13

Reaction of: EG and $NH_3$
Reaction Temperature: 183° C.
Reaction Time: 0.5 hours; $NH_3$ Charge: 2.56 g; EG Charge: 22.265 g
$H_2$ Pressure at 25° C.: 545 psig; EG:$NH_3$ Molar Ratio: 2.36:1
Results:

| Product | Weight (grams) | Selectivity NH₃ Conversion 3% | EG Conversion 4% |
|---|---|---|---|
| MELA | 0.03 | 10 | 3 |
| DELA | 0.00 | 0 | 0 |
| TELA | 0.00 | 0 | 0 |
| HEP | 0.00 | 0 | 0 |
| BHEP | 0.00 | 0 | 0 |

Catalyst: $Ru_3(CO)_{12}$ (100 mg); Reactor: 50 cc Pressure Bomb

EXAMPLE 14

Reaction of: EG and $NH_3$
Reaction Temperature: 222° C.
Reaction Time: 0.5 hours; $NH_3$ Charge: 2.32 g; EG Charge: 22.03 g
$H_2$ Pressure at 25° C.: 540 psig; EG:$NH_3$ Molar Ratio: 2.60:1
Results:

| Product | Weight (grams) | Selectivity NH₃ Conversion 48% | EG Conversion 30% |
|---|---|---|---|
| MELA | 0.69 | 17 | 11 |
| DELA | 2.59 | 38 | 46 |
| TELA | 0.38 | 4 | 7 |
| HEP | 0.27 | 6 | 6 |
| BHEP | 0.80 | 14 | 17 |

Catalyst: $Ru_3(CO)_{12}$ (100 mg); Reactor: 50 cc Pressure Bomb

EXAMPLE 15

Reaction of: EG and $NH_3$
Reaction Temperature: 200° C.
Reaction Time: 2 hours; $NH_3$ Charge: 5.985 g; EG Charge: 49.922 g
$H_2$ Pressure at 25° C.: 510 psig; EG:$NH_3$ Molar Ratio: 2.29:1
Results:

| Product | Weight (grams) | Selectivity NH₃ Conversion 80% | EG Conversion 71% |
|---|---|---|---|
| MELA | 1.59 | 9 | 5 |
| DELA | 7.13 | 24 | 24 |
| TELA | 4.28 | 10 | 15 |
| HEP | 0.50 | 3 | 2 |
| BHEP | 5.19 | 21 | 21 |

Catalyst: $Ru_3(CO)_{12}$ (100 mg); Reactor: 175 cc Autoclave

EXAMPLE 16

Reaction of: EG and $NH_3$
Reaction Temperature: 200° C.
Reaction Time: 2 hours; $NH_3$ Charge: 6.26 g; EG Charge: 11.01 g
$H_2$ Pressure at 25° C.: 500 psig; EG:$NH_3$ Molar Ratio: 0.48:1
Results:

| Product | Weight (grams) | Selectivity NH₃ Conversion 22% | EG Conversion 26% |
|---|---|---|---|
| MELA | 0.92 | 19 | 33 |
| DELA | 0.36 | 4 | 15 |
| TELA | 0.00 | 0 | 0 |
| HEP | 0.25 | 5 | 13 |
| BHEP | 0.05 | 1 | 3 |

Catalyst: $Ru_3(CO)_{12}$ (125 mg); Reactor: 50 cc Pressure Bomb

EXAMPLE 17

Reaction of: EG and $NH_3$
Reaction Temperature: 203° C.
Reaction Time: 2 hours; $NH_3$ Charge: 5.36 g; EG Charge: 10.8 g
$H_2$ Pressure at 25° C.: 550 psig; EG:$NH_3$ Molar Ratio: 0.55:1
Results:

| Product | Weight (grams) | Selectivity NH₃ Conversion 31% | EG Conversion 12% |
|---|---|---|---|
| MELA | 0.55 | 9 | 44 |
| DELA | 0.10 | 1 | 9 |
| TELA | 0.00 | 0 | 0 |
| HEP | 0.03 | 1 | 10 |
| BHEP | 0.01 | 0 | 1 |

Catalyst: $Ru_3(CO)_{12}$ (100 mg); Reactor: 50 cc Pressure Bomb

EXAMPLE 18

Reaction of: EG and $NH_3$
Reaction Temperature: 203° C.
Reaction Time: 2 hours; $NH_3$ Charge: 6.45 g; EG Charge: 10.834 g
$H_2$ Pressure at 25° C.: 545 psig; EG:$NH_3$ Molar Ratio: 0.46:1
Results:

|         |         | Selectivity |         |
|---------|---------|-------------|---------|
|         |         | NH₃         | EG      |
|         | Weight  | Conversion  |         |
| Product | (grams) | 30%         | 15%     |
| MELA    | 0.68    | 10          | 43      |
| DELA    | 0.14    | 1           | 10      |
| TELA    | 0.00    | 0           | 0       |
| HEP     | 0.11    | 1           | 9       |
| BHEP    | 0.01    | 0           | 1       |

Catalyst: $Ru_3(CO)_{12}$ (100 mg); Reactor: 50 cc Pressure Bomb

EXAMPLE 19

Reaction of: EG and $NH_3$
Reaction Temperature: 202° C.
Reaction Time: 2 hours; $NH_3$ Charge: 5.29 g; EG Charge: 10.88 g
$H_2$ Pressure at 25° C.: 520 psig; EG:$NH_3$ Molar Ratio: 0.56:1
Results:

|         |         | Selectivity |         |
|---------|---------|-------------|---------|
|         |         | NH₃         | EG      |
|         | Weight  | Conversion  |         |
| Product | (grams) | 30%         | 21%     |
| MELA    | 0.77    | 14          | 34      |
| DELA    | 0.27    | 3           | 14      |
| TELA    | 0.01    | 0           | 1       |
| HEP     | 0.18    | 3           | 11      |
| BHEP    | 0.03    | 0           | 2       |

Catalyst: $Ru_3(CO)_{12}$ (100 mg); Reactor: 50 cc Pressure Bomb

EXAMPLE 20

Reaction of: EG and $NH_3$
Reaction Temperature: 203° C.
Reaction Time: 2 hours; $NH_3$ Charge 14.4 g; EG Charge: 27.02 g
$H_2$ Pressure at 25° C.: 520 psig; EG:$NH_3$ Molar Ratio: 0.51:1
Results:

|         |         | Selectivity |         |
|---------|---------|-------------|---------|
|         |         | NH₃         | EG      |
|         | Weight  | Conversion  |         |
| Product | (grams) | 63%         | 55%     |
| MELA    | 2.60    | 8           | 18      |
| DELA    | 1.97    | 4           | 16      |
| TELA    | 0.11    | 0           | 1       |
| HEP     | 1.01    | 3           | 10      |
| BHEP    | 0.75    | 2           | 7       |

Catalyst: $Ru_3(CO)_{12}$ (250 mg); Reactor: 175 cc Autoclave

EXAMPLE 21

Reaction of: EG and $NH_3$
Reaction Temperature: 203° C.
Reaction Time: 2 hours; $NH_3$ Charge: 14.4 g; EG Charge: 27.02 g
$H_2$ Pressure at 25° C.: 520 psig; EG:$NH_3$ Molar Ratio: 0.52:1
Results:

|         |         | Selectivity |         |
|---------|---------|-------------|---------|
|         |         | NH₃         | EG      |
|         | Weight  | Conversion  |         |
| Product | (grams) | 68%         | 64%     |
| MELA    | 2.41    | 7           | 14      |
| DELA    | 1.90    | 3           | 13      |
| TELA    | 0.09    | 0           | 1       |
| HEP     | 1.23    | 3           | 10      |
| BHEP    | 1.03    | 2           | 9       |

Catalyst: $Ru_3(CO)_{12}$ (250 mg); Reactor: 175 cc Autoclave

EXAMPLE 22

Reaction of: EG and $NH_3$
Reaction Temperature: 233° C.
Reaction Time: 4 hours; $NH_3$ Charge: 14.54 g; EG Charge: 27 g
$H_2$ Pressure at 25° C: 510 psig; EG:$NH_3$ Molar Ratio: 0.51:1
Results:

|         |         | Selectivity |         |
|---------|---------|-------------|---------|
|         |         | NH₃         | EG      |
|         | Weight  | Conversion  |         |
| Product | (grams) | 65%         | 87%     |
| MELA    | 0.81    | 2           | 3       |
| DELA    | 0.36    | 1           | 2       |
| TELA    | 0.02    | 0           | 0       |
| HEP     | 1.05    | 3           | 6       |
| BHEP    | 0.57    | 1           | 3       |

Catalyst: $Ru_3(CO)_{12}$ (250 mg); Reactor: 50 cc Pressure Bomb

Examples 23–26 demonstrate the relationship between EG:$NH_3$ charge ratio and the amount of nitrogen-containing alkyl product produced. This data is graphically depicted in FIG. 6. Despite indications of inefficient and incomplete mixing in the 50 cc pressure bomb reactor, the linear relationship is clearly evident.

EXAMPLE 23

Reaction of: EG and $NH_3$
Reaction Temperature: 203° C.
Reaction Time: 2 hours; $NH_3$ Charge: 6.45 g; EG Charge: 10.834 g
$H_2$ Pressure at 25° C.: 545 psig; EG:$NH_3$ Molar Ratio: 0.46:1
Results:

|         |         | Selectivity |         |
|---------|---------|-------------|---------|
|         |         | NH₃         | EG      |
|         | Weight  | Conversion  |         |
| Product | (grams) | 30%         | 15%     |
| MELA    | 0.68    | 10          | 43      |
| DELA    | 0.14    | 1           | 10      |
| TELA    | 0.00    | 0           | 0       |
| HEP     | 0.11    | 1           | 9       |
| BHEP    | 0.01    | 0           | 1       |

Catalyst: $Ru_3(CO)_{12}$ (100 mg); Reactor: 50 cc Pressure Bomb

EXAMPLE 24

Reaction of: EG and $NH_3$
Reaction Temperature: 203° C.

Reaction Time: 2 hours; NH$_3$ Charge: 5.36 g; EG Charge: 10.8 g
H$_2$ Pressure at 25° C.: 550 psig; EG:NH$_3$ Molar Ratio: 0.55:1
Results:

| Product | Weight (grams) | Selectivity NH$_3$ Conversion 31% | EG Conversion 12% |
|---|---|---|---|
| MELA | 0.55 | 9 | 44 |
| DELA | 0.10 | 1 | 9 |
| TELA | 0.00 | 0 | 0 |
| HEP | 0.09 | 1 | 10 |
| BHEP | 0.01 | 0 | 1 |

Catalyst: Ru$_3$(CO)$_{12}$ (100 mg); Reactor: 50 cc Pressure Bomb

EXAMPLE 25

Reaction of: EG and NH$_3$
Reaction Temperature: 202° C.
Reaction Time: 2 hours; NH$_3$ Charge: 3.83 g; EG Charge: 10.76 g
H$_2$ Pressure at 25° C.: 525 psig; EG:NH$_3$ Molar Ratio: 0.77:1
Results:

| Product | Weight (grams) | Selectivity NH$_3$ Conversion 63% | EG Conversion 55% |
|---|---|---|---|
| MELA | 0.68 | 33 | 26 |
| DELA | 0.36 | 10 | 16 |
| TELA | 0.00 | 0 | 0 |
| HEP | 0.12 | 5 | 7 |
| BHEP | 0.04 | 1 | 2 |

Catalyst: Ru$_3$(CO)$_{12}$ (100 mg); Reactor: 50 cc Pressure Bomb

EXAMPLE 26

Reaction of: EG and NH$_3$
Reaction Temperature: 203° C.
Reaction Time: 2 hours; NH$_3$ Charge: 2.93 g; EG charge: 10.59 g
H$_2$ Pressure at 25° C.: 520 psig; EG:NH$_3$ Molar Ratio: 0.99:1
Results:

| Product | Weight (grams) | Selectivity NH$_3$ Conversion 23% | EG Conversion 3% |
|---|---|---|---|
| MELA | 0.19 | 8 | 56 |
| DELA | 0.01 | 0 | 3 |
| TELA | 0.00 | 0 | 0 |
| HEP | 0.01 | 0 | 4 |
| BHEP | 0.00 | 0 | 0 |

Catalyst: Ru$_3$(CO)$_{12}$ (100 mg); Reactor: 50 cc Pressure Bomb

EXAMPLE 27

Reaction of: EG and NH$_3$
Reaction Temperature: 202° C.
Reaction Time: 2 hours; NH$_3$ Charge: 1.82 g; EG Charge: 10.71 g
H$_2$ Pressure at 25° C.: 530 psig; EG:NH$_3$ Molar Ratio: 1.61:1
Results:

| Product | Weight (grams) | Selectivity NH$_3$ Conversion 31% | EG Conversion 33% |
|---|---|---|---|
| MELA | 0.50 | 25 | 14 |
| DELA | 1.08 | 31 | 36 |
| TELA | 0.13 | 3 | 5 |
| HEP | 0.23 | 11 | 9 |
| BHEP | 0.40 | 14 | 16 |

Catalyst: Ru$_3$(CO)$_{12}$ (100 mg); Reactor: 50 cc Pressure Bomb

EXAMPLE 28

Reaction of: EG and NH$_3$
Reaction Temperature: 202° C.
Reaction Time: 2 hours; NH$_3$ Charge: 4.91 g; EG Charge: 10.64 g
H$_2$ Pressure at 25° C.: 540 psig; EG:NH$_3$ Molar Ratio: 0.59:1
Results:

| Product | Weight (grams) | Selectivity NH$_3$ Conversion 32% | EG Conversion 35% |
|---|---|---|---|
| MELA | 0.99 | 17 | 27 |
| DELA | 0.67 | 7 | 21 |
| TELA | 0.02 | 0 | 1 |
| HEP | 0.31 | 5 | 12 |
| BHEP | 0.15 | 2 | 6 |

Catalyst: Ru$_3$(CO)$_{12}$ (100 mg); Reactor: 50 cc Pressure Bomb

EXAMPLE 29

Reaction of: EG and NH$_3$
Reaction Temperature: 203° C.
Reaction Time: 2 hours; NH$_3$ Charge 12 g; EG Charge: 44.4 g
H$_2$ Pressure at 25° C.: 510 psig; EG:NH$_3$ Molar Ratio: 1.01:1
Results:

| Product | Weight (grams) | Selectivity NH$_3$ Conversion 26% | EG Conversion 45% |
|---|---|---|---|
| MELA | 3.73 | 33 | 19 |
| DELA | 2.81 | 15 | 17 |
| TELA | 0.18 | 1 | 1 |
| HEP | 1.15 | 10 | 8 |
| BHEP | 1.24 | 8 | 9 |

Catalyst: Ru$_3$(CO)$_{12}$ (250 mg); Reactor: 175 cc Autoclave

EXAMPLE 30

Reaction of: EG and NH$_3$
Reaction Temperature: 203° C.

Reaction Time: 2 hours; NH₃ charge: 5.56 g; EG Charge: 10.92 g
H₂ Pressure at 25° C.: 515 psig; EG:NH₃ Molar Ratio: 0.54:1
Results:

| Product | Weight (grams) | Selectivity NH₃ Conversion 27% | EG Conversion 24% |
|---|---|---|---|
| MELA | 0.87 | 16 | 33 |
| DELA | 0.38 | 4 | 17 |
| TELA | 0.01 | 0 | 0 |
| HEP | 0.22 | 4 | 12 |
| BHEP | 0.04 | 1 | 2 |

Catalyst: Ru₃(CO)₁₂ (100 mg); Reactor: 50 cc Pressure Bomb

EXAMPLE 31

Reaction of: EG and NH₃
Reaction Temperature: 202° C.
Reaction Time: 2 hours; NH₃ Charge: 5.29 g; EG Charge: 10.88 g
H₂ Pressure at 25° C.: 520 psig; EG:NH₃ Molar Ratio: 0.56:1
Results:

| Product | Weight (grams) | Selectivity NH₃ Conversion 30% | EG Conversion 21% |
|---|---|---|---|
| MELA | 0.77 | 14 | 34 |
| DELA | 0.27 | 3 | 14 |
| TELA | 0.01 | 0 | 1 |
| HEP | 0.18 | 3 | 11 |
| BHEP | 0.03 | 0 | 2 |

Catalyst: Ru₃(CO)₁₂ (100 mg); Reactor: 50 cc Pressure Bomb

EXAMPLE 32

Reaction of: EG and NH₃
Reaction Temperature: 202° C.
Reaction Time: 2 hours; NH₃ Charge: 3.76 g; EG Charge: 10.41 g
H₂ Pressure at 25° C.: 535 psig; EG:NH₃ Molar Ratio: 0.76:1
Results:

| Product | Weight (grams) | Selectivity NH₃ Conversion 33% | EG Conversion 21% |
|---|---|---|---|
| MELA | 0.61 | 14 | 29 |
| DELA | 0.29 | 4 | 16 |
| TELA | 0.00 | 0 | 0 |
| HEP | 0.18 | 4 | 12 |
| BHEP | 0.05 | 1 | 3 |

Catalyst: Ru₃(CO)₁₂ (100 mg); Reactor: 50 cc Pressure Bomb

EXAMPLE 33

Reaction of: EG and NH₃
Reaction Temperature: 202° C.
Reaction Time: 2 hours; NH₃ Charge: 2.9 g; EG Charge: 10.73 g
H₂ Pressure at 25° C.: 545 psig; EG:NH₃ Molar Ratio: 1.01:1
Results:

| Product | Weight (grams) | Selectivity NH₃ Conversion 36% | EG Conversion 29% |
|---|---|---|---|
| MELA | 0.63 | 17 | 21 |
| DELA | 0.70 | 11 | 27 |
| TELA | 0.02 | 0 | 1 |
| HEP | 0.25 | 6 | 12 |
| BHEP | 0.20 | 4 | 9 |

Catalyst: Ru₃(CO)₁₂ (100 mg); Reactor: 50 cc Pressure Bomb

EXAMPLE 34

Reaction of: EG and NH₃
Reaction Temperature: 203° C.
Reaction Time: 2 hours; NH₃ Charge: 1.45 g; EG Charge: 10.71 g
H₂ Pressure at 25° C.: 535 psig; EG:NH₃ Molar Ratio: 2.02:1
Results

| Product | Weight (grams) | Selectivity NH₃ Conversion 37% | EG Conversion 29% |
|---|---|---|---|
| MELA | 0.28 | 14 | 9 |
| DELA | 1.04 | 31 | 40 |
| TELA | 0.17 | 4 | 7 |
| HEP | 0.22 | 11 | 10 |
| BHEP | 0.41 | 15 | 19 |

Catalyst: Ru₃(CO)₁₂ (100 mg); Reactor: 50 cc Pressure Bomb

EXAMPLE 35

Reaction of: EG and NH₃
Reaction Temperature: 203° C.
Reaction Time: 2 hours; NH₃ Charge: 14.4 g; EG Charge: 27.02 g
H₂ Pressure at 25° C.: 520 psig; EG:NH₃ Molar Ratio: 0.51:1
Results:

| Product | Weight (grams) | Selectivity NH₃ Conversion 63% | EG Conversion 55% |
|---|---|---|---|
| MELA | 2.60 | 8 | 18 |
| DELA | 1.97 | 4 | 16 |
| TELA | 0.11 | 0 | 1 |
| HEP | 1.01 | 3 | 10 |
| BHEP | 0.75 | 2 | 7 |

Catalyst: Ru₃(CO)₁₂ (250 mg); Reactor: 175 cc Autoclave

EXAMPLE 36

Reaction of: EG and NH₃
Reaction Temperature: 202° C.

Reaction Time: 2 hours; NH$_3$ Charge: 4.91 g; EG Charge: 10.64 g
H$_2$ Pressure at 25° C.: 540 psig; EG:NH$_3$ Molar Ratio: 0.59:1
Results:

| Product | Weight (grams) | Selectivity | |
|---|---|---|---|
| | | NH$_3$ Conversion 63% | EG Conversion 55% |
| MELA | 0.99 | 17 | 27 |
| DELA | 0.67 | 7 | 21 |
| TELA | 0.02 | 0 | 1 |
| HEP | 0.31 | 5 | 12 |
| BHEP | 0.15 | 2 | 6 |

Catalyst: Ru$_3$(CO)$_{12}$ (100 mg); Reactor: 50 cc Pressure Bomb

EXAMPLE 37

Reaction of: EG and NH$_3$
Reaction Temperature: 203° C.
Reaction Time: 2 hours; NH$_3$ Charge: 14.4 g; EG Charge: 27.02 g
H$_2$ Pressure at 25° C.: 520 psig; EG:NH$_3$ Molar Ratio: 0.52:1
Results:

| Product | Weight (grams) | Selectivity | |
|---|---|---|---|
| | | NH$_3$ Conversion 68% | EG Conversion 64% |
| MELA | 2.41 | 7 | 14 |
| DELA | 1.90 | 3 | 13 |
| TELA | 0.09 | 0 | 1 |
| HEP | 1.23 | 3 | 10 |
| BHEP | 1.09 | 2 | 9 |

Catalyst: Ru$_3$(CO)$_{12}$ (250 mg); Reactor: 175 cc Autoclave

EXAMPLE 38

Reaction of: EG and NH$_3$
Reaction Temperature: 200° C.
Reaction Time: 2 hours; NH$_3$ Charge: 2.41 g; EG Charge: 22.04 g
H$_2$ Pressure at 25° C.: 535 psig; EG:NH$_3$ Molar Ratio: 2.50:1
Results:

| Product | Weight (grams) | Selectivity | |
|---|---|---|---|
| | | NH$_3$ Conversion 54% | EG Conversion 44% |
| MELA | 0.67 | 14 | 7 |
| DELA | 3.70 | 46 | 45 |
| TELA | 1.08 | 9 | 14 |
| HEP | 0.22 | 4 | 3 |
| BHEP | 1.64 | 24 | 24 |

Catalyst: H$_4$Ru$_4$(CO)$_{12}$ (87 mg); Reactor: 175 cc Autoclave

EXAMPLE 39

A brief series of trials using other second and third row carbonyl complexes indicated that the order of catalytic activity (in the absence of hydrogen) is:

Ru$_3$(CO)$_{12}$~H$_4$Ru$_4$(CO)$_{12}$>>Os$_3$(CO)$_{12}$>Ir$_4$(CO)$_{12}$>Rh$_6$(CO)$_{16}$~Re$_2$(CO)$_{10}$

No optimization of conditions for the non-Ru catalysts was attempted, although all carbonyl catalyst precursors used performed better under hydrogen pressures.

In the foregoing descriptions and examples, Ru$_3$(CO)$_{12}$ is referred to as a catalyst for the subject reactions, since this compound is added to the reactor. It should be noted that these, as well as other catalysts employed, may not necessarily exert their catalytic activity in this form, but may serve as precursors for the actual compound or complex formed in the reaction medium under operating conditions. The term "catalyst" as employed herein, will be understood to include both precursors and active catalysts formed therefrom.

While this invention has been described with reference to specific examples, it will nontheless be understood by those skilled in the art that other variations of process conditions, catalysts, and parameters may be employed without departing from the true spirit of the invention. It is intended that the claims which follow should be construed to encompass all such variations.

STATEMENT OF INDUSTRIAL UTILITY

The present invention comprises a novel process for the synthesis of hydroxyalkyl amines, hydroxyalkyl piperazines, or alkyl piperazines from ammonia and alkylene glycols using a periodic table row 2 or row 3-metal substantially soluble catalyst system.

What is claimed is:

1. A process for the synthesis of hydroxyalkyl amines, hydroxyalkyl piperazines, or alkyl piperazines from an alkyl amine or ammonia and an alkylene glycol by reacting said ammonia or alkyl amine and said alkylene glycol in the presence of a substantially soluble catalyst, said catalyst being derived from a catalyst precursor selected from the group of the carbonyl complexes of ruthenium, osmium, iridium, rhodium and rhenium.

2. The synthetic process of claim 1 wherein said alkyl amine is a primary, secondary, or tertiary amine having from 1 to 24 carbon atoms.

3. The synthetic process of claim 1 wherein said alkyl amine is a primary, secondary, or tertiary amine having from 1 to 8 carbon atoms.

4. The synthetic process of claim 1 wherein said alkylene glycol contains from 2 to 4 carbon atoms.

5. The synthetic process of claim 1 wherein said reaction is carried out at a temperature of from 150° C. to 300° C.

6. The synthetic process of claim 1 wherein said reaction is carried out at a temperature of from 180° C. to 230° C.

7. The synthetic process of claim 1 wherein said reaction is carried out at a temperature of from 200° C. to 220° C.

8. The synthetic process of claim 1 wherein said reaction is carried out under a hydrogen atmosphere at a pressure of from about 0 psig to 1000 psig.

9. The synthetic process of claim 1 wherein said reaction is carried out under a hydrogen atmosphere at a pressure of from 250 psig to 750 psig.

10. The synthetic process of claim 1 wherein the molar ratio of said glycol species to said amine species or said ammonia is from 1:3 to 10:1.

11. The synthetic process of claim 1 wherein the molar ratio of said glycol species to said amine species or said ammonia is from 1:3 to 3:1.

12. The synthetic process of claim 1 wherein the molar ratio of said glycol species to said amine species or said ammonia is from 0.5:1 to 2.5:1.

13. A process for the synthesis of hydroxyalkyl amines, hydroxyalkyl piperazines, or alkyl piperazines from an alkyl amine or ammonia and an alkylene glycol by reacting said ammonia or alkyl amine and said alkylene glycol in the presence of a substantially soluble catalyst, said catalyst being derived from a catalyst precursor selected from the group of $Ru_3(CO)_{12}$, $H_4Ru_4(CO)_{12}$, $Os_3(CO)_{12}$, $Ir_4(CO)_{12}$, $Rh_6(CO)_{16}$, and $Re_2(CO)_{10}$, and salts thereof.

14. A process for the synthesis of hydroxyalkyl amines, hydroxyalkyl piperazines, or alkyl piperazines from an alkyl amine or ammonia and an alkylene glycol by reacting said ammonia or alkyl amine and said alkylene glycol in the presence of a substantially soluble catalyst, said catalyst being derived from a catalyst precursor being a carbonyl complex of ruthenium.

15. The synthetic process of claim 14 wherein said alkyl amine is a primary, secondary, or tertiary amine having from 1 to 24 carbon atoms.

16. The synthetic process of claim 14 wherein said alkylene glycol contains from 2 to 4 carbon atoms.

17. The synthetic process of claim 14 wherein said reaction is carried out at a temperature of from 150° C. to 300° C.

18. The synthetic process of claim 14 wherein said reaction is carried out at a temperature of from 200° C. to 220° C.

19. The synthetic process of claim 14 wherein said reaction is carried out under a hydrogen atmosphere at a pressure of from about 0 psig to 1000 psig.

20. The synthetic process of claim 14 wherein the molar ratio of said glycol species to said amine species or said ammonia is from 1:3 to 10:1.

21. A process for the synthesis of hydroxyalkyl amines, hydroxyalkyl piperazines, or alkyl piperazines from an alkyl amine or ammonia and an alkylene glycol by reacting said ammonia or alkyl amine and said alkylene glycol in the presence of a substantially soluble catalyst, said catalyst being derived from a catalyst precursor selected from the group of $Ru_3(CO)_{12}$ and $H_4Ru_4(CO)_{12}$ and salts thereof.

22. The synthetic process of claim 21 wherein said reaction is carried out at a temperature of from 200° C. to 220° C.

* * * * *